| United States Patent [19] | [11] Patent Number: 5,344,923 |
|---|---|
| Verma et al. | [45] Date of Patent: Sep. 6, 1994 |

[54] NUCLEOTIDE SEQUENCE ENCODING FOR BIFUNCTIONAL ENZYME FOR PROLINE PRODUCTION

[75] Inventors: Desh P. S. Verma, Powell; Chien-an A. Hu, Columbus, both of Ohio; Ashton J. Delauney, St. Thomas, Barbados

[73] Assignee: The Ohio State University Research Foundation, Columbus, Ohio

[21] Appl. No.: 953,695

[22] Filed: Sep. 29, 1992

[51] Int. Cl.$^5$ ...................... C07H 17/00; C12N 15/00
[52] U.S. Cl. .................. 536/23.2; 536/23.6; 435/172.3
[58] Field of Search .............. 800/205; 536/23.2, 23.6, 536/23.4; 435/172.3

[56] References Cited

U.S. PATENT DOCUMENTS 4,594,323  6/1986  Csonica et al. .................. 435/107

OTHER PUBLICATIONS

Hemon et al. 1990. Plant Mol. Biol. 15:895–904.
Delauney et al. 1990. Plant Mol. Biol. Manual A14:1–23.
Weisemann et al. Jul. 1991. Conference Abstract, 8th Annual Mid-Atlantic Plant Molecular Biology Society Mtg., p. 35.
Miao et al., "Ammonia-Regulated Expression of a Soybean Gene Encoding Cytosolic Glutamine Synthetase in Transgenic *Lotus corniculatus*" *The Plant Cell,* vol. 3, 1991, pp. 11–22.
Csonka, "Physiological and Genetic Responses of Bacteria to Osmotic Stress", *Microbiol. Rev.,* vol. 53, No. 1, 1989, pp. 121–147.
Krueger et al., "Purification to Homogeneity of Pyrroline-5Reductase of Barley", *Plant Physiol.,* vol. 80, 1986, pp. 142–144.
Rhodes et al., "Metabolic Chnages Associated with Adaptation of Plant Cells to Water Stress", *Plant Physiol.,* vol. 82, 1986, pp. 890–903.
Rayapati et al., "Pyrroline-5-Carboxylate Reductase Is in Pea (*Pisum sativum* L.) Leaf Chloroplasts", *Plant Physiol.,* vol. 91, 1989, 581–586.
Delauney et al., "A soybean gene encoding 1-pyrroline-5-carboxylate reductase was isolated by functional complementation in *Escherichia coli* and is found to be osmoregulated", *Mol. Gen. Genet.,* vol. 221, 1990, pp. 299–305.
Verbruggen et al., "Isolation and Charactertization of 1-Pyrroline-5-carboxylate Reductase Genes from Arabidopsis Thaliana", Abstract, Third Intl. Congress, Intl. Soc. for Plant Mol. Biology, Tucson, Ariz. Oct. 6–11, 1991.
Hayzer et al., "The Gene-Enzyme Relationships of Proline Biosynthesis in *Escherichia coli*", *J. Gen. Microbiol.,* vol. 118, 1980, pp. 287–293.
Delauney et al., "Isolation of plant genes by heterologous complementation in *Escherichia coli*", *Plant Molecular Biology Manual,* Kluwer Academic Publishers, Dordrech, 1990, pp. A14:1–22.
Verwoerd et al., "A small-scale procedure for the rapid isolation of plant RNAs", *Nucl. Acids Res.,* vol. 17, No. 6, 1989, p. 2362.
Kohl et al., "Proline metabolism in $N_2$-fixing root nodules: Energy transfer and regulation of purine synthesis", *Proc. Natl. Acad. Sci USA,* vol. 85, 1988, pp. 2036–2040.
Deutch et al., "*Escherichia coli* $^1$-pyrroline-5-carboxylate reductase: gene sequence, protein overproduction (List continued on next page.)

*Primary Examiner*—David T. Fox
*Assistant Examiner*—Elizabeth C. Kemmerer
*Attorney, Agent, or Firm*—Frank H. Foster

[57] ABSTRACT

The invention is directed to the isolation and identification of a mothbean (*Vigna aconitifolia*) cDNA clone encoding a bifunctional enzyme, delta$^1$-pyrroline-5-carboxylate synthetase, hereinafter P5CS, with both gamma-glutamyl kinase and glutamic-gamma-semialdehyde dehydrogenase activities that catalyzes the first two steps in plant proline production, also called biosynthesis.

2 Claims, 8 Drawing Sheets

OTHER PUBLICATIONS and purification", *Nucl. Acids Res.*, vol. 10, No. 23, 1982, pp. 7701 et seq.

Tomenchok et al., "Gene-Enzyme Relationships in the Proline Biosynthetic Pathway of *Saccharomyces cerevisiae*", *J. of Bacteriology*, vol. 169, No. 12, 1987, pp. 5364–5372.

Le Rudulier et al., "Genetic engineering in agriculture: osmoregulation", *Trends Biochem. Sci.*, vol. 7, 1982, p. 431.

Le Rudulier et al., "Nitrogen Fixation in Klebsiella Pneumoniae During Osmotic Stress Effect of Exogenous Proline or a Proline Overproducing Plasmid", *Biochim. Biophys. Acta*, vol. 719, 1982, pp. 273–283.

Le Rudulier et al., "Molecular Biology of Osmoregulation", *Science*, vol. 224, 1984, pp. 1064–1068.

Jones et al., "High level expression of introduced chimaeric genes genes in regenerated transformed plants", *Embo J.*, vol. 4, No. 10, 1985, pp. 2411–2418.

Gubler et al., "A simple and very efficient method for generating cDNA libraries", *Gen*, vol. 25, 1983, pp. 263–269.

Mahmoudi et al., "Comparison of Two Different Hybridization Systems in Northern Transfer Analysis", *Biotechniques*, vol. 7, No. 4, 1989, pp. 331–333.

Delauney et al., "A stable bifunctional antisense transcript inhibiting gene expression in transgenic plants", *Proc. Nat. Acad. Sci. USA*, vol. 85, 1988, pp. 4300–4304.

Snustad et al., "Maize Glutamine Synthetase cDNAs: Isolation by Direct Genetic Selection in *Escherichia coli*", *Genetics*, vol. 120, 1988, pp. 1111–1124.

DeSarma et al., "Plant Glutamine Synthetase Complements a glnA Mutation in *Escherichia coli*", *Science*, vol. 232, 1986, pp. 1242–1244.

Hu et al., "A novel bifunctional enzyme ($^1$-pyrroline-5-carboxylate synthetase) catalyzes the first two steps in proline biosynthesis in plants", manuscript submitted for publication in Oct. 1992 in *Proc. Natl. Acad. Sci.*

Verma et al., "Genetic manipulation for proline overproduction and the control of osmoregulation in plants", manuscript prepared but as yet unpublished.

FIG. 1A

```
TGCTCTAAAGGCTATTGCTCTCGTATCAGTGCTCTCAGCCATGGAGAGCGCGGTGGATCCTTCTCG
                                  M  E  S  A  V  D  P  S  R
                                     ProB →

CGCGAAGAAGGAAGGTTAGCGGTTGGAAGATTGGGAGCTCTGTGCCAGCAGATTAAGCAACT
 R  E  E  G  R  L  A  V  G  R  L  G  A  L  C  E  Q  I  K  Q  L

CAAAGGCTACGTTTCCGTAATTAATCAACAGCAGCTTCGCCGACCTTCAGAAACCCCAACT
 Q  R  L  R  F  R  K  L  I  N  S  F  A  D  L  Q  K  P  Q  L

GATACGCTGTTCACTCAGCTCGATGTGACATCGGCTCAGCTTCTTGTGACGGATAACGATTT
 D  T  L  F  T  Q  L  D  V  T  S  A  Q  L  L  V  T  D  N  D  F

AAGGTTATTCCGGTGTTCAATGAGAACGATGCCGTTAGTACCAGGAAGGCTCCCTATGAGGA
 K  V  I  P  V  F  N  E  N  D  A  V  S  T  R  K  A  P  Y  E  D

AAAGCCCGATCTCCTTGTTTTGTTGAGTGATGTAGAAGGTCTTTACAGTGGCCCTCCAAGTGA
 K  A  D  L  L  V  L  L  S  D  V  E  G  L  Y  S  G  P  P  S  D

TTTGGCGACAAGTCTAGAGTGGGAAGAGGCCGAATGACTGCCAAAGTAAAAGCTGCGGTTCA
 F  G  D  K  S  R  V  G  R  G  G  M  T  A  K  V  K  A  A  V  H

ATTAATGTTCTCCAAGGACAACGTATAGAACTCTCTTCCATAAAGATGCACATGAGTGGGC
 I  N  V  L  Q  G  Q  R  I  G  T  L  F  H  K  D  A  H  E  W  A

GGCTCCAGGCCGTTATCTTCAGAGGAAAAGGAAACAAAATTTACTTAAAATAGCTGATGCCCT
 G  S  R  R  Y  L  Q  R  K  G  N  K  I  L  L  K  I  A  D  A  L

GAAGCAGGATATGAAAAATCCTTGGTGGCTAGCTTTAAAACCTGGGAAGATTGCAAG
 E  A  G  Y  E  K  S  L  V  A  R  L  A  L  K  P  G  K  I  A  S
```

FIG. 1B

```
GGGGTTCATGAAGGACGTGAAGCGTGTGATCATCAAAGTTGGCACCGCGGGTGGTCACT    120
 G  F  M  K  D  V  K  R  V  I  I  K  V  G  T  A  V  V  T       28

CAACTCTCTCGGATACGACATTATACTCGTCTCCTCTGGCCCCCGTCGTATTGGACGC      240
 N  S  L  G  Y  D  I  I  L  V  S  S  G  P  V  G  I  G  R       68

CGAACTCGACGGCCAAGGCCTGCGCCGCCGTTGGAGACAGAACAGTCTCATGGCTCTCTAC   360
 E  L  D  G  K  A  C  A  A  V  G  Q  N  S  L  M  A  L  Y       108

TCGAGATAAGGATTTCAGGAAGCAGCTTACTGAGACTGTGAAGTCGCTGTTGGCGCTG      480
 R  D  K  D  F  R  K  Q  L  T  E  T  V  K  S  L  L  A  L       148

TTCTTCTGGTATATTTGGGATAATGATAGTTTATCTGCTTTATTAGCCTTGGAGTTA       600
 S  S  G  I  F  W  D  N  D  S  L  S  A  L  L  A  L  E  L       188

CCCTCATTCAAAGCTTATTTATACATATAACAAAGAAAACATCAGAATGAAATTACT       720
 P  H  S  K  L  I  Y  T  Y  N  K  E  K  H  Q  N  E  I  T       228

TGCAGCTGAAGCTGGCATTCCTGTTGTTATTACCAGTGGTTTTGCACCTGAGAATATC      840
 A  A  E  A  G  I  P  V  V  I  T  S  G  F  A  P  E  N  I       268

TCAAGTAAAAGAGGTTGATGCACGTGAGATGGCTGTTGCAGCAGGGAATGTTCGAGAA      960
 Q  V  K  E  V  D  A  R  E  M  A  V  A  A  G  N  V  R  E       308
                            ProA→

GGAAGCAAATGAAAAATAATCAGGATTGAAAATGAAGCTGATGTTACTGCTGCACAA      1080
 E  A  N  E  K  I  I  R  I  E  N  E  A  D  V  T  A  A  Q       348

TCTTGCAAACAACATGGAATCATTGCCAATATGGAAGATCCAATTGGTCGAGTATTA      1200
 L  A  N  N  M  R  I  I  A  N  M  E  D  P  I  G  R  V  L       388
```

FIG. 1C

```
AAACGTACCGAGCTTTCAGATGGGCTAATTTTAGAAAAGACATCATCTCCTTTGGGAGTGCT
 K  R  T  E  L  S  D  G  L  I  L  E  K  T  S  S  P  L  G  V  L

CGAAGTGGGAATGGGCTTCTCTCTTGAAAGGTGGCTAAGAAGCTAAGCGATCAAATGCAATTT
 R  S  G  N  G  L  L  L  K  G  G  K  E  A  K  R  S  N  A  I  L

GTGACCTCAAGGGAAGAGATCCCTGAGCTACTTAAGTTGGATGATGTAATTGATCTGGTAAT
 V  T  S  R  E  E  I  P  E  L  L  K  L  D  D  V  I  D  L  V  I

TTAGGTCATGCTGATGGAATTGCCATGTCTATGTTGATAAGTCTGCTAACGTGGAGATGGC
 L  G  H  A  D  G  I  C  H  V  Y  V  D  K  S  A  N  V  E  M  A

ACACTTCTTATCCACAAGGATTTGATGAGTAGTCATGAGTTCGCTGCTTGCACCGCCGAAATTGTGGA
 T  L  L  I  H  K  D  L  I  E  K  G  W  L  K  E  I  I  L  D  L

CCACAAGCACATTCATTTCATCATGAGTACAGTTCGCTGCTTGCACCGCCGAAATTGTGGA
 P  Q  A  H  S  F  H  H  E  Y  S  S  L  A  C  T  A  E  I  V  D

ATCGTTGCTGAAGATAACGAAGTAGCTAATGTGTTTCTACGCCAAGTAGACAGTGCTGCTGT
 I  V  A  E  D  N  E  V  A  N  V  F  L  R  Q  V  D  S  A  A  V

GGTTGGAATTAGTACAAGCAGGATTCATGCTCGAGGTCAGTAGGAGTTGAGGATTGTTAACA
 G  W  N  *
CACCCACAAAGACCTTGCAATTAATTTAATGTGCTTTGATTCCTTTTGTAGCCTTTCG
AATTTATGTCATTATTGCTTGTTCCTTTTTGTCTAGAATCTTTTACTGTCAACAATTATGT
GTAAAAAAAAAAAA
```

FIG. 1D

```
CCTTATTGTTTTTGAGTCACGTCCTGATGCTCTCTTGTACAGATAGCTTCATTGGCAATC  1320
 L  I  V  F  E  S  R  P  D  A  L  V  Q  I  A  S  L  A  I        428

GCACAAAGTAATTATCGAGGCCATACCAGATAATGTTGGTGGAAAACTTATAGGACTT    1440
 H  K  V  I  E  A  I  P  D  N  V  G  G  K  L  I  G  L           468

TCCAAGAGGCAGTAACAAACTTGTTTCTCAGATCAAGAGTTCAACTAAAATTCCTGTT    1560
 P  R  G  S  N  K  L  V  S  Q  I  K  S  S  T  K  I  P  V        508

AAAGCGGATTGTATTAGATGCAAAAGTTGATTATCCGGCAGCCTGCAATGCCATGGAA    1680
 K  R  I  V  L  D  A  K  V  D  Y  P  A  A  C  N  A  M  E        548

TCGAACTGAAGGCGTTATATTATATGGTGGCCCTGTGGCAAGTTCTCTGTTAAATATT    1800
 R  T  E  G  V  I  L  Y  G  G  P  V  A  S  S  L  L  N  I        588

TGACGTGTATGCAGCTATTGATCATATAAATCTGTATGGAAGTGCACATACTGATTCG    1920
 D  V  Y  A  A  I  D  H  I  N  L  Y  G  S  A  H  T  D  S        628

TTTTCACAATGCAAGCACCAGATTCAGTGATGGGCACGATTGAGACTAGGCGCAGA      2040
 F  H  N  A  S  T  R  F  S  D  G  A  R  F  E  T  R  R  R        668

ACAAGATGGATACTAAAAGGAAGGAAGTGGTAGATGGTGATAGAGGCGTTGTCTA        2160
                                                                671
TTTGTTTTTTTTTTCACAGTAGAGAACGGCATTTGTACGGTTAATAAACCGGGT         2280
CCACAATGTTAACGATTCTTGAATGACTACACAATTTCAATTTGAGTTAATTTTTATAT   2400
                                                                2417
```

```
VPBA  12 MKDVKRVIIKVGTAVVTREEGRLAVGRLGALCEQIKQLNSLGYDIILVSS  61
         |.| . :::|:||.|:| :. ||. :::..|. |. ||:. |. |::|.|
EPB    1 MSDSQTLVVKLGTSVLTGGSRRLNRAHIVELVRQCAQLHAAGHRIVIVTS  50

VPBA  62 GPVGIGRQRLRFRKLINSSFADLQKPQLELDGKACAAVGQNSLMALYDTL 111
         |::: ||::| :...|       |.:...||       |||||..|:.|:: |
EPB   51 GAIAAGREHLGYPELP....ATIASKQLL......AAVGQSRLIQLWEQL  90

VPBA 112 FTQLDVTSAQLLVTDNDFRDKDFRKQLTETVKSLLALKVIPVFNENDAVS 161
         |. ..:: :|:|:| .||: |::   .:|::.||. .::||:|||||.
EPB   91 FSIYGIHVGQMLLTRADMEDRERFLNARDTLRALLDNNIVPVINENDAVA 140

VPBA 162 TRKAPYEDSSGIFWDNDSLSALLALELKADLLVLLSDVEGLY.SGPPSDP 210
         |   . :    |||.|||| |:      || |:||.| .||| .:|.|:|
EPB  141 TAAIKVG.......DNDNLSALAAILAGADKLLLLTDQKGLYTADPRSNP 183

VPBA 211 HSKLI.YTYNKEKHQNEITFGDKSRVGRGGMTAKVKAAVHAAEAGIPVVI 259
         :..|| .|.. :.   ..|. :. | :| |||..|:.|| |. |||..:|
EPB  184 QAELIKDVYGIDDALRAIARDSVSGLGTGGMSTKLQAADVACRAGIDTII 233

VPBA 260 TSGFAPENIINVLQGQRIGTLFHKDAHEWAQVKEVDAREMAVAAGNVREG 309
         ..| |: | :|::| .:||||| :| .:.. |   . :.:. .| ||
EPB  234 AAGSKPGVIGDVMEGISVGTLFHAQATPLENRKRWIFGAPPAGEITVDEG 283

VPBA 310 SRRYLQRKGNKILLKIADALEAN...EKIIRIENEADVTAAQEAGYEKSL 356
         . : :|..:|| |  ...:.:|   :.:|||   |.: . |:::.: .|
EPB  284 ATAAILERGSSLLPKGIKSVTGNFSRGEVIRICNLEGRDIAHGVSRYNS. 332

VPBA 357 VARLALKPGKIASLANNMRIIANMEDPIGRVLKRTELSDGLILEKTSSPL 406
                                    |:: |: : . . : ||: . :|:
EPB  333 ......................DALRRIAGHHSQEIDAILGYEYGPV 357

VPBA 407 GVLLIVFESRPDALV 421
         :|        :.|.::
EPB  358 AV.......HRDDMI 365
```

FIG. 2B

```
B
VPBA  298 EMAVAAGNVREGSRRYLQRKGNKILLKIADALEANEKIIRIENEADVTAA 347
          :|::||  ...    .. |. |::| ||||.|||...|| .|..||..|
 EPA    4 QMGIAAKQASYKLAQLSSREKNRVLEKIADELEAQSEIILNANAQDVADA  53

VPBA  348 QEAGYEKSLVARLALKPGKIASLANNMRIIANMEDPIGRVLKRTELSDGL 397
          ...|.......::.||||.|:::  ::|:::| :.|:.||:|.|:. . |..||
 EPA   54 RANGLSEAMLDRLALTPARLKGIADDVRQVCNLADPVGQVIDGGVLDSGL 103

VPBA  398 ILEKTSSPLGVLLIVFESRPDALVQIASLAIRSGNGLLLKGGKEAKRSNA 447
          ||: . ||||: :::|.||:. |:::|||.::.||:::|||||. |.||
 EPA  104 RLERRRVPLGVIGVIYEARPNVTVDVASLCLKTGNAVILRGGKETCRTNA 153

VPBA  448 ILHKVIIEAIPD.NVGGKLIGLV.[TSREE]IPELLKLDDVIDLVIPRGSN 494
          ||  :|:..  .:.:   :. :    ..|. :.|:|:::|.  ||::||||:.
 EPA  154 ATVAVIQDALKSCGLPAGAVQAIDNPDRALVSEMLRMDKYIDMLIPRGGA 203

VPBA  495 KLVSQIKSSTKIPVLGHADGICHVYVDKSANVEMAKRIVLDAKVDYPAAC 544
          |  ..:. ..|||:. : |:||:|||.|.:::.  |  ::::::||.:  |..|
 EPA  204 GLHKLCREQSTIPVITGGIGVCHIYVDESVEIAEALKVIVNAKTQRPSTC 253

VPBA  545 NAMETLLIHK[DLIEKGWLKEIILDLRTEGVIL]YGGPVASSLLNIP..... 589
          |.:||||::|: |..::|..: ::  ..||.|.::::.| . |.. 
 EPA  254 NTVETLLVNKN.IADSFLPALSKQMAESGVTLHADAAALAQLQAGPAKVV 302

VPBA  590 ..QAHSFHHEYSSLACTAEIVDDVYAAIDHINLYGSAHTDSIVAEDNEVA 637
          .|..:..|:  ||.  ...||.|: .||.||. .|...|.|.|:.
 EPA  303 AVKAEEYDDEFLSLDLNVKIVSDLDDAIAHIREHGTQHSDAILT...... 346

VPBA  638 NVFLRQVDSAAVFHNASTRFSDGARFE  664
          |:: .|. | |||||||.||:.|:
 EPA  347 ....RDMRNAQRFVNASTRFTDGGQFG  369
```

Bacteria
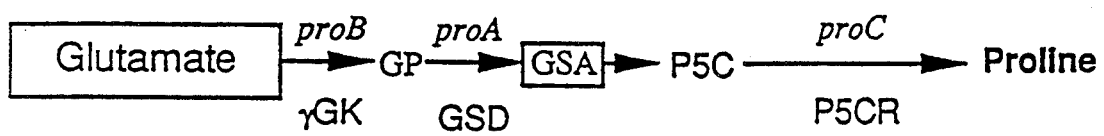
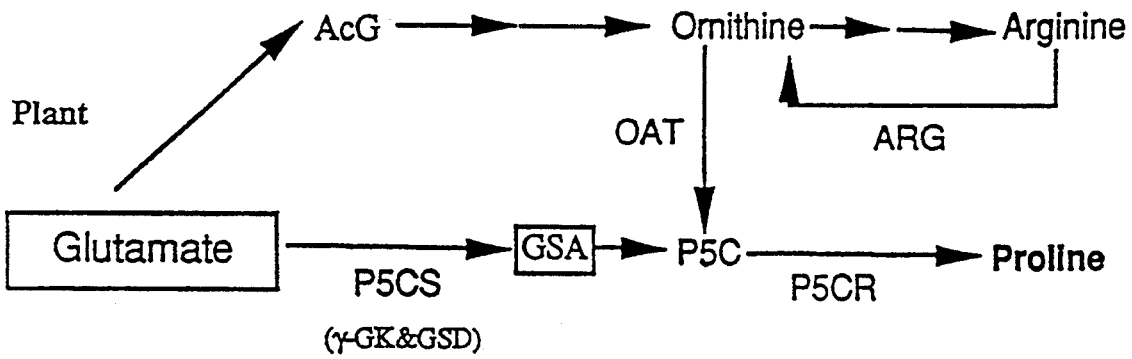
FIG. 4

1

NUCLEOTIDE SEQUENCE ENCODING FOR BIFUNCTIONAL ENZYME FOR PROLINE PRODUCTION

TECHNICAL FIELD

The invention relates to a novel bifunctional enzyme which catalyzes the first two steps in proline production in plants leading to osmoregulation in the plants.

BACKGROUND ART

Many plants synthesize and accumulate proline in response to osmotic stress. Drought and high salinity are the most important environmental factors that cause osmotic stress and impact negatively on plant growth and crop productivity. The role of proline biosynthesis in osmoregulation in bacteria is well established in, for example, Csonka, *Microbiol. Rev.* 53, 1989, pp. 121–147. The proline biosynthesis route in plants is not as well known but is thought to follow the biosynthesis route in bacteria. In *Escherchia coli*, the synthesis starts with the phosphorylation of glutamate by gamma-glutamyl kinase, hereinafter gamma-GK, which is encoded by the proB gene. The gamma-glutamyl phosphate thus formed is reduced to glutamic-gamma-semialdehyde, hereinafter GSA, by GSA dehydrogenase (GSD) which is encoded by the proA gene. The GSA thus produced spontaneously cyclizes to delta$^1$-pyrroline-5-carboxylate (P5C) which is delta$^1$-pyrroline-5-carboxylate reductase, hereinafter P5CR, which is encoded by the proC gene, to thereby form proline.

With the exception of P5CR which has been recently characterized (Krueger et al., *Plant Physiol.*, 82, 1986, pp. 890–903; Rayapati et al., *Plant Physiol.*, 91, 1989, pp. 581–586; Delauney and Verma, *Mol. Gen. Genet.*, 221, 1990, pp. 299–305; Verbruggen et al., Abstract, Third International Congress, International Society for Plant Molecular Biology, Tucson, Ariz., Oct. 6–11, 1991), however, little is known about the other enzymes in this pathway in plants.

Therefore, it would be desirable to use genetic engineering of the proline production pathway in plants to counter osmotic stress to alter the level of a known osmoprotectant to thereby lead to a significant enhancement of crop performance under conditions of salt and drought stress.

BRIEF DISCLOSURE OF INVENTION

The invention is directed to the isolation and identification of a mothbean (*Vigna aconitifolia*) cDNA clone encoding a bifunctional enzyme, delta$^1$-pyrroline-5-carboxylate synthetase, hereinafter P5CS, with both gamma-glutamyl kinase and glutamic-gamma-semialdehyde dehydrogenase activities that catalyzes the first two steps in plant proline production, also called biosynthesis. By "bifunctional" herein is meant the ability of a single enzyme to perform two different catalyses and encode for gamma-GK and GSD.

The present invention was achieved by direct complementation of specific *E. coli* mutants with a Vigna nodule cDNA expression library. The isolated cDNAs have been fused to a strong plant promoter, and transferred to plants by Agrobacterium-mediated transformation. Transgenic Vigna roots have demonstrated overproduction of proline.

It is one object of the present invention to provide the complete nucleotide sequence of a P5CS cDNA clone, pVAB2.

Another object of the present invention is to provide a cDNA clone encoding a bifunctional enzyme, i.e., an enzyme that catalyzes both gamma-GK and GSD.

Yet another object of the present invention is to provide a method to overproduce proline and thus increase sodium chloride tolerance and drought resistance in a plant by the introduction into the plant of the P5CS cDNA clone encoding a bifunctional enzyme that catalyzes both gamma-GK and GSA production in said plant.

Yet another object of the present invention is to provide a method to increase glutamine synthetase (GS) activity in plants, thereby increasing the amount of substrate available for P5CS (glutamate) in the production of proline.

BRIEF DESCRIPTION OF THE FIGURES

In describing the preferred embodiment of the invention, which is illustrated in the FIGURES, specific terminology will be resorted to for the sake of clarity. However, it is not intended that the invention be limited to the specific terms so selected and it is to be understood that each specific term includes all technical equivalents which operate in a similar manner to accomplish a similar purpose. The words used to describe the invention are not literal limitations but include elements recognized as being equivalent by those skilled in the art.

FIG. 1 is the complete nucleotide sequence of a P5CS cDNA clone, pVAB2, and primary sequence of the encoded *V. aconitifolia* delta$^1$-pyrroline-5-carboxylate synthetase. The polypeptide region homologous to the *E. coli* gamma-GK (ProB) domain is underlined. The carboxy half of P5CS corresponds to GSA dehydrogenase (ProA).

FIG. 2 is a comparison of the *V. aconitifolia* P5CS amino acid sequence with A) the *E. coli* gamma-GK and B) GSA dehydrogenase sequences. Identical amino acids are indicated by a vertical line and similar amino acids are indicated by colons and periods. The conserved aspartic acid residues implicated in proline feedback inhibition are boxed, as are the leucine zipper sequences and the potential phosphorylation sites.

FIG. 4 illustrates the proline synthetic pathways in bacteria and plants, starting from glutamate. In bacteria, separate proB and proA steps are found for encoding gamma-GK and GSD, respectively, to produce GSA, whereas in plants, the glutamate is converted directly to GSA by the bifunctional enzyme, P5CS.

DETAILED DESCRIPTION

Figure 3:
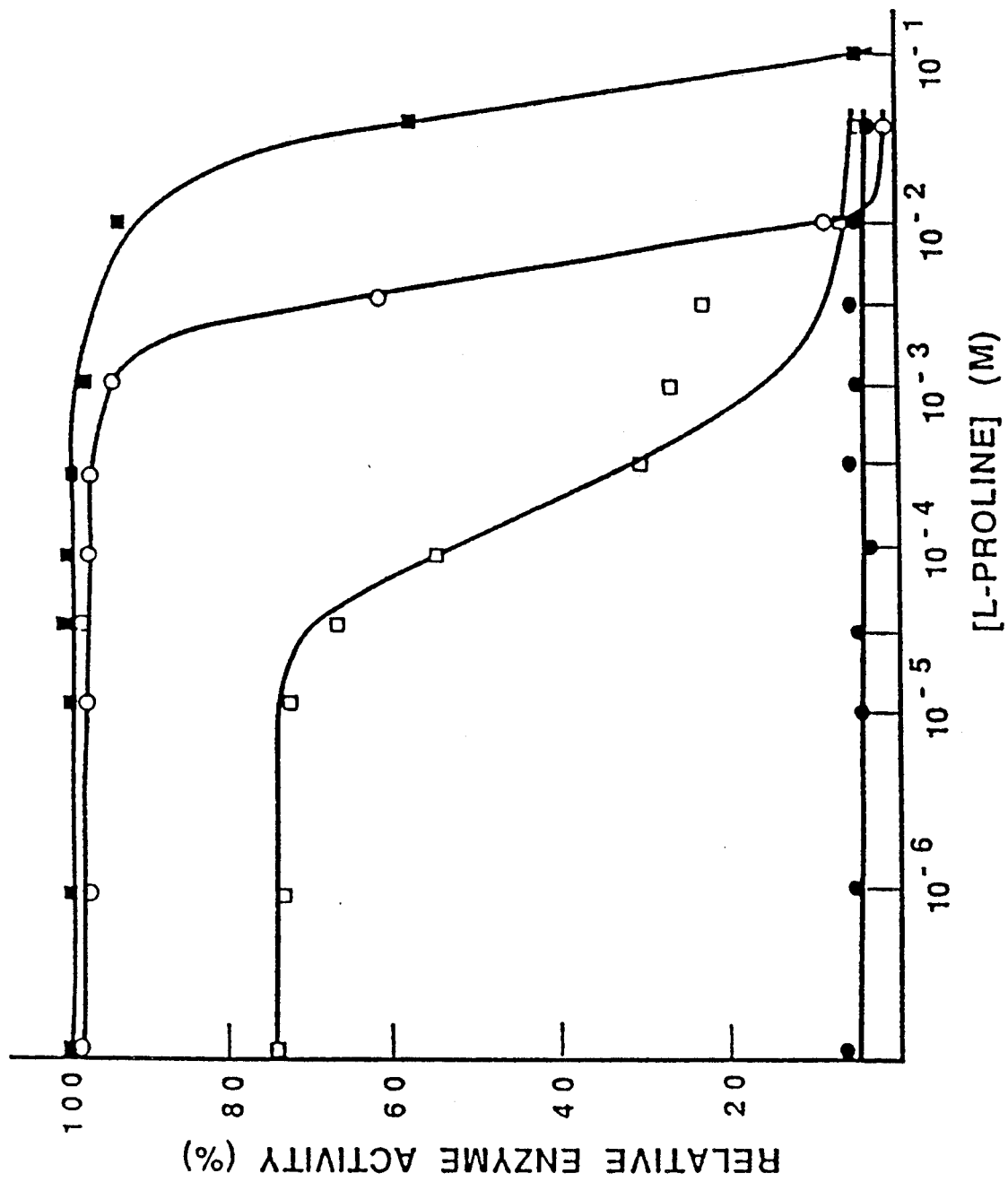
FIG. 3 is a graph illustrating feedback inhibition of delta$^1$-pyrroline-5-carboxylate synthetase by proline. Ammonium sulfate-fractionated extracts from *E. coli* CSH26 (●), *E. coli* CSH26 harboring pVAB2 (o), the proB74 allele (■), and the wild-type proB allele (□) were assayed for gamma-GK activity by the method of Hayzer and Leisinger, *J. Gen. Microbiol.*, 118, 1980, pp. 287–293.

By the present invention, *E. coli* proB, proA, and proBA auxotrophic mutants were transformed by electroporation with a *Vigna aconitifolia* nodule cDNA expression library. A transformation efficiency of $10^9$–$10^{10}$ transformants/ug of DNA was routinely obtained by the present invention, which is about two orders of magnitude higher than that obtained by classical transformation methods. Thus electroporation significantly enhances the recovery of complemented mutants. One group of clones of the present invention was isolated by selection for growth of transformants on minimal media without proline. It has been determined by the present invention that these clones encode a novel bifunctional enzyme, P5CS, which has both gamma-GK and GSD activities. The P5CS clones produced according to the present invention efficiently complemented E. coli proB, proA, and proBA, but not proC mutants. The predicted amino acid sequence of the enzyme produced by the present invention revealed the presence of two domains with significant homology to the E. coli proA and proB proteins. The recombinant P5CS protein of the present invention demonstrated GSD-dependent gamma-GK enzyme activity.

The complete nucleotide sequence of a P5CS cDNA clone, pVAB2, is shown in FIG. 1. The 2417 bp sequence contains a single major open reading frame encoding a polypeptide of 73.2kD, assuming that translation is initiated at the first ATG codon from the 5' end of the coding strand. Sequence comparison with the E. coli ProB and ProA proteins (FIG. 2) indicate that V. aconitifolia P5CS polypeptide has two distinct domains. The amino terminal domain of the P5CS protein showed 33.3% identity and 55.5% overall similarity to the E. coli ProB protein. A domain with 35.7% identity and 57.9% similarity to the ProA protein is located at the carboxyl end of the nucleotide sequence. An unexpectedly high level (42.4%) of the sequence similarity was found between the E. coli ProB and ProA proteins leading the inventor to the conclusion that the proB and proA of an ancestral gene; the encoded proteins may have later acquired domains conferring the respective kinase and reductase activities of the present-day enzymes. It has been surprisingly discovered in the present invention that the corresponding plant genes have evidently fused to create the bifunctional enzyme identified herein from V. aconitifolia.

FIG. 4 illustrates the comparison between the proline production pathways in bacteria and plants and the genes involved. The key difference is the fusion or merging of the proB and proA catalytic steps of the bacteria into the single gene in the plant pathway to form GSA. Both the bacteria and the plant proline production pathways start with glutamate, then proceed through GSA to P5C which, in the presence of P5CR, is converted or reduced to proline. However, in bacteria, the glutamate is phosphorylated in the presence of gamma-GK encoded by proB to produce glutamyl phosphate (GP). The GP is then converted to GSA by GSD encoded by proA. In the plant, however, it has been discovered herein that the glutamate is converted directly to GSA by the bifunctional enzyme P5CS, shown in FIG. 1. The P5CS therefore has the combined properties of proB and proA in the proline synthetic pathway.

Interestingly, it has also been discovered herein that a "leucine zipper" sequence (see FIG. 2) is present in each of the enzymatic domains of Vigna P5CS. The leucine zippers mediate protein:protein dimerization in structural proteins of both eucaryotes and procaryotes as well as in transcriptional regulatory proteins. It is believed that the leucine zippers in P5CS function intramolecularly to maintain the proper tertiary structure of the two domains of this enzyme, and homodimer or heterodimer formation may occur through the leucine zippers to allow close association between the originally separate enzymes (proB and proA) fused in P5CS. It is also possible that these zippers are a relic of the time when the gamma-GK and GSA-dehydrogenase enzymes were separate and had to be brought together to form a functional complex, as in E. coli. Thus these leucine zippers may facilitate inter- intra-molecular interactions. In addition, P5CS contains a potential phosphorylation site (FIG. 2). P5CS has GSA dehydrogenase and gamma-GK activities, and the gamma-GK activity is feedback inhibited by proline. To confirm that the presently claimed sequence, pVAB2 of FIG. 1, encoded P5CS activity, ammonium sulfate-fractionated extracts of E. coli CSH26 and CSH26 harboring pVAB2 were assayed for GSA dehydrogenase-dependent gamma-GK enzyme activity. As shown by the essentially horizontal line (●) in FIG. 3, no gamma-GK activity was detected in E. coli strain CSH26, whereas CSH26 containing pVAB2 exhibited a high level of gamma-GK activity (see curve (o)). Because proline production is regulated by end-product inhibition of gamma-GK in bacteria, the plant enzyme P5CS was similarly subjected to feed-back control testing. FIG. 3 shows that the Vigna enzyme is 50% inhibited by 6 mM proline. The wild-type E. coli gamma-GK (see curve (□) of FIG. 3) was 30 times more sensitive than the Vigna enzyme, i.e., it shows 50% inhibition at 0.2 mM proline, while a mutant form of the bacterial enzyme (encoded by the proB74 allele, curve (■)) is approximately 200-fold less sensitive to end product inhibition. Thus, the sensitivity of the recombinant Vigna enzyme (curve (o)) to feedback inhibition is much less than that of the wild-type E. coli enzyme (curve (□)) but more than that of the mutated gamma-GK enzyme. The mutation responsible for the resistance to end-product inhibition of the gamma-GK in the proB 74 allele involves a substitution of an A for a G nucleotide, resulting in a change from aspartic acid to asparagine residue at position 107. It is to be noted, however, that this aspartate residue is conserved in the Vigna P5CS enzyme of the present invention, raising the possibility that changing this residue to asparagine by site-directed mutagenesis may result in further diminution of feedback inhibition of the plant enzyme. In spite of the conserved aspartic acid residue implicated in feedback control, the Vigna enzyme is less sensitive to inhibition by proline than is the E. coli enzyme suggesting that other regions of the P5CS enzyme may also be important for feedback regulation.

By observing the sensitivity of the mothbean enzyme to end-product inhibition in proline synthesis, it has been discovered in the present invention that regulation of the pathway in plants is exerted primarily at the P5CS step.

To demonstrate the expression levels of the Vigna P5CS gene in different tissues and under conditions of osmotic stress, RNA from nodules, leaves, and roots, as well as roots from plants watered with 200 mM sodium chloride, was probed on a northern blot with the pVAB2 cDNA. The results showed that the P5CS transcript in Vigna leaves was more abundant than in the roots and nodules. The level of P5CS transcripts in roots was enhanced by treatment of the plant with 200 mM sodium chloride. An increase in the level of transcript of P5CS and P5CR during osmotic stress will therefore facilitate increased proline production from glutamate.

To demonstrate that P5CR activity is not a rate limiting step in proline production in plants, the soybean P5CR cDNA was placed under the control of cauliflower mosaic virus (CaMV-35S) promoter and introduced into Vigna via T-DNA mediated transformation. Regenerated plants showed 10 to 100 fold increase in the amount of P5CR activity in the leaves. Measurement of proline and P5C levels in the transgenic plants indicated that proline synthesis was limited by P5C production rather than the activity of P5CR. All P5C in control and transgenic plants was converted to proline. No significant accumulation of proline occurred in transgenic plants expressing high levels of P5CR because the specific activity of the P5CR of both stressed and unstressed Vigna cell cultures is hundreds of folds greater than the proline synthesis rate, and the enzyme of the present invention functions at only a small fraction of its $V_{max}$. Therefore, P5CR is not rate limiting in the proline production pathway in plants.

Using the procedures described in Miao et al., The Plant Cell, Vol. 3, January 1991, pp. 11–12, the isolated cDNA of the present invention was transferred into transgenic Vigna plants to demonstrate the effect therein on proline production. Table I illustrates a comparison of control versus transgenic Vigna plants. The results illustrate that the proline content of the control plants (samples 1, 2 and 3) was low (0.76 to 2.42 micromoles of proline per gram of root tissue) relative to the proline content of the transgenic Vigna plants of the present invention (samples 4–8), i.e. 3.9 to 13.2 micromoles of proline per gram of root tissue. This represents a 10 to 100 fold increase in proline production in the transgenic plants as a result of the transference of the nucleotide sequence of the present invention.

TABLE I

Concentrations of proline in control and transgenic Vigna roots

| Sample Number | Tissue (hairy roots) | ug proline/g of fresh root | uM proline/g of fresh root |
|---|---|---|---|
| 1 | Control (wt-1) | 11 | 0.76 |
| 2 | Control (wt-2) | 22.2 | 1.54 |
| 3 | Control (wt-3) | 35 | 2.42 |
| 4 | AH30-A7 | 160 | 11.08 |
| 5 | AH30-10 | 190 | 13.2 |
| 6 | AH30-B12 | 170 | 11.8 |
| 7 | AH30-C8 | 56 | 3.9 |
| 8 | AH30-55 | 130 | 9.0 |

Control tissue was obtained from roots transformed with pB1121 only.

Thus, the invention provides a method of inducing both P5CS and P5CR genes by salt stress. The cloned plant gene of the present invention encodes the two enzymes in the plant which catalyze the first two reaction steps in the production of proline, long believed to provide a crucial role in osmoregulation. As demonstrated by the present invention, it is now possible to remove feedback control on proline production in plants and to produce the overexpression of proline from P5CS to confer salt and drought tolerance on a crop plant.

The invention further relates to increasing GS activity in plants thereby increasing the amount of substrate available for P5CS (glutamate) in the production of proline. This increase is achieved by introduction to the plant of the GS gene obtained by the procedures described in Miao et al., The Plant Cell, Vol. 3, January 1991, pp. 11–12. By this invention, the GS activity in the plant is increased relative to the level before introduction of the GS gene, whereby proline production is increased.

EXPERIMENTAL

Bacterial Growth Conditions

E. coli mutant cells were grown at 37 degrees Centigrade in LB medium or in Minimal A medium (see Delauney and Verma, Plant Molecular Biology Manual, Kluwer Academic Publishers, Dordrecht, 1990, pp. A14: 1–22) supplemented with 0.2 mM of required amino acids and 0.05 mM of thiamine. Ampicillin was added at 100 mg/l. The osmotic medium was increased by the addition of NaCl as indicated.

Plasmids and Bacterial Strains

Plasmids carrying wild-type proB (pDU1) and mutant proB74 (pDU101) allele were obtained from A. Dandekar (University of California, Davis). E. coli strains #X340, #W4032, #CSH26 and #X342 were obtained from B. Bachman, E. coli Genetics Stock Center, Yale University.

Construction of cDNA Expression Library

RNA was prepared from 21 day old mothbean (Vigna aconitifolia, L.) nodules by the method of Verwoerd et al., Nucl. Acid Res., 17, 1989, p. 2362, and poly(A)+ RNA was isolated by chromatography on an oligo(dT)-cellulose column. Double stranded cDNA was synthesized, ligated to BstXI linkers, and size-fractionated on an agarose gel. Molecules greater than 500 bp in size were electroeluted from the gel, cloned into the BstXI-linearized pcDNAII plasmid vector (Invitrogen Corp., San Diego, Calif., and E. coli DHIα cells were transformed. cDNA molecules inserted within the polylinkers of pcDNAII in the correct orientation and reading frame can be expressed under the control of the lacZ promoter.

Functional Complementation of E. coli Auxotrophs

E. coli proline auxotrophs were transformed by electroporation using Electro Cell Manipulator 600 apparatus (BTX, San Diego, Calif.) according to the manufacturers instructions. Briefly, cells were grown to late log phase in LB broth, pelleted by centrifugation, washed twice in ice-cold 10% glycerol in water solution, resuspended in cold 10% glycerol, and stored in 200 ul aliquots at −80° C. For electroporation, 20 ng of the pooled library DNA purified by double cesium chloride centrifugation was added to 200 ul of competent cells in a 2 mm cuvette and subjected to a 5 msec pulse at 2.5 kV/cm. The cells were immediately added to 10 ml of LB broth and incubated at 37° C. with shaking for 1 hour. The cells were then pelleted by centrifugation, washed with Minimal A medium, and plated into Minimal A plates containing ampicillin (100 ug/ml), IPTG (1 mM) and the amino acid supplements other than proline required by the respective mutants. To determine the transformation efficiencies, aliquots of electroporated cells were plated on the same media supplemented with proline (1 mM). Plates were incubated at 37° C. for two days. Plasmid DNA, prepared from single colonies grown in minimal media containing ampicillin, was used to retransform the mutants to confirm the complementation.

DNA Sequencing and Analysis

DNA sequencing was performed on CsCl-purified, double-stranded plasmid DNA by the dideoxynucleotide chain termination method using Sequenase II (U.S.

Biochemicals, Cleveland, Ohio) according to the manufacturer's instructions. Deletions of the plasmid template were generated using Exonuclease III and mungbean nuclease.

P5CS Enzyme Assay and Determination of End-product Feedback Inhibition

E. coli CSH26 cells and CSH26 harboring different plasmids were grown aerobically at 37° C. for about 16 hours. The cells were harvested by centrifugation at 4,000×g for 10 minutes, and the cell paste resulting was suspended in 4 ml of buffer A (50 mM Tris-HCl 1 mM dithiothreitol) at 40° C. Following sonication, (Benson Sonifier, Type 450) at 50 watts, the slurry was centrifuged at 4,000×g for 10 minutes and the supernatant fractionated by ammonium sulfate precipitation. For E. coli CSH26 containing pVAB2, the fraction precipitating between 0 and 30% saturation of ammonium sulfate was used for enzyme assay. The E. coli CSH26 and CSH26 harboring the proB74 or wild-type proB alleles, a fraction of 40 to 60% saturation was used. Ammonium sulfate precipitated fraction was dissolved in buffer A and dialyzed against the same buffer. Gamma-GK activity was assayed as a function of proline concentration (0.01 to 100 mM) to determine if proline synthesis is subject to end-product inhibition in plants.

Northern Blot Analysis

Poly(A)+RNA from mothbean nodules, leaves and roots, as well as roots from plants watered with 200 mM NaCl, were electrophoresed in a 1.2% agarose-2.2M formaldehyde gel and transferred by vacuum blotting to a Gene Screen membrane (DuPont NEN, Boston, Mass.). The pVAB2 cDNA insert was labeled with $^{32}$P-dCTP to a specific activity of $8 \times 10^8$ dpm/ug using a random primer labeling system (Amersham, Arlington Heights, Ill). Hybridization was performed by the method of Delauney and Verma, *Mol. Gen. Genet.*, 221, 1990, pp. 299–305, and filters were exposed to x-ray film at −70° C.

While certain preferred embodiments of the present invention have been disclosed in detail, it is to be understood that various modifications may be adopted without departing from the spirit of the invention or scope of the following claims.

---

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 2417 base pairs
        ( B ) TYPE: nucleic acid
        ( C ) STRANDEDNESS: double stranded
        ( D ) TOPOLOGY: linear ( i i ) MOLECULE TYPE: cDNA
        ( A ) DESCRIPTION: Sequence encodes Pyrroline-5-carboxylate synthetase, a bifunctional enz ( v ) FRAGMENT TYPE:
        N-terminus: N-MESAVDPS-- C-terminus: --RRRGWN-C
        Internal Fragment: --VDAREMAV--

( v i ) ORIGINAL SOURCE:
        ( A ) ORGANISM: Vigna aconitifolia
        ( B ) STRAIN: Mothbean
        ( D ) DEVELOPMENTAL STAGE: Root nodules ( v i i ) IMMEDIATE SOURCE:
        ( A ) LIBRARY: cDNA expression library
        ( B ) CLONE: cDNA clone ( x ) PUBLICATION INFORMATION:
        ( A ) AUTHORS: Chien-An A. Hu, Ashton J. Delauney and Desh Pal S. Verma
        ( B ) TITLE: A bifunctional enzyme (delta1-pyrroline-5-carboxylate synthetase) catalyzes t
        ( C ) JOURNAL: Proceeding of the National Academy of Science USA
        ( D ) VOLUME: 89
        ( E ) ISSUE: October
        ( F ) PAGES: 9354-9358
        ( G ) DATE: OCT-1992
        ( K ) RELEVANT RESIDUES IN SEQ ID NO: 1: FROM position 37 to position 2049 GenBank M9227

( x i ) SEQUENCE DESCRIPTION: SEQ ID NO: 1:

```
TGCTCTAAAG GCTATTGCTC GTATCAGTGC TCAGCC ATG GAG AGC GCG           4 8
                                        Met Glu Ser Ala
                                        1
```

-continued

| | | | | | | | | | | | | | | | | |
|---|---|---|---|---|---|---|---|---|---|---|---|---|---|---|---|---|
|GTG|GAT|CCT|TCT|CGG|GGG|TTC|ATG|AAG|GAC|GTG|AAG|CGT|GTG|ATC|ATC|96|
|Val|Asp|Pro|Ser|Arg|Gly|Phe|Met|Lys|Asp|Val|Lys|Arg|Val|Ile|Ile| |
|5| | | |10| | | | |15| | | | |20| | |
|AAA|GTT|GGC|ACC|GCG|GTG|GTC|ACT|CGC|GAA|GAA|GGA|AGG|TTA|GCG|GTT|144|
|Lys|Val|Gly|Thr|Ala|Val|Val|Thr|Arg|Glu|Glu|Gly|Arg|Leu|Ala|Val| |
|25| | | |30| | | | |35| | | | | | | |
|GGA|AGA|TTG|GGA|GCT|CTG|TGC|GAG|CAG|ATT|AAG|CAA|CTC|AAC|TCT|CTC|192|
|Gly|Arg|Leu|Gly|Ala|Leu|Cys|Glu|Gln|Ile|Lys|Gln|Leu|Asn|Ser|Leu| |
|40| | | |45| | | | |50| | | | | | | |
|GGA|TAC|GAC|ATT|ATA|CTC|GTC|TCC|TCT|GGC|CCC|GTC|GGT|ATT|GGA|CGC|240|
|Gly|Tyr|Asp|Ile|Ile|Leu|Val|Ser|Ser|Gly|Pro|Val|Gly|Ile|Gly|Arg| |
|55| | | |60| | | | |65| | | | | | | |
|CAA|AGG|CTA|CGT|TTC|CGT|AAA|TTA|ATC|AAC|AGC|AGC|TTC|GCC|GAC|CTT|288|
|Gln|Arg|Leu|Arg|Phe|Arg|Lys|Leu|Ile|Asn|Ser|Ser|Phe|Ala|Asp|Leu| |
|70| | | |75| | | | |80| | | | | | | |
|CAG|AAA|CCC|CAA|CTC|GAA|CTC|GAC|GGC|AAG|GCC|TGC|GCC|GCC|GTT|GGA|336|
|Gln|Lys|Pro|Gln|Leu|Glu|Leu|Asp|Gly|Lys|Ala|Cys|Ala|Ala|Val|Gly| |
|85| | | |90| | | | |95| | | | | |100| |
|CAG|AAC|AGT|CTC|ATG|GCT|CTC|TAC|GAT|ACG|CTG|TTC|ACT|CAG|CTC|GAT|384|
|Gln|Asn|Ser|Leu|Met|Ala|Leu|Tyr|Asp|Thr|Leu|Phe|Thr|Gln|Leu|Asp| |
|105| | | |110| | | | |115| | | | | | | |
|GTG|ACA|TCG|GCT|CAG|CTT|CTT|GTG|ACG|GAT|AAC|GAT|TTT|CGA|GAT|AAG|432|
|Val|Thr|Ser|Ala|Gln|Leu|Leu|Val|Thr|Asp|Asn|Asp|Phe|Arg|Asp|Lys| |
|120| | | |125| | | | |130| | | | | | | |
|GAT|TTC|AGG|AAG|CAG|CTT|ACT|GAG|ACT|GTG|AAG|TCG|CTG|TTG|GCG|CTG|480|
|Asp|Phe|Arg|Lys|Gln|Leu|Thr|Glu|Thr|Val|Lys|Ser|Leu|Leu|Ala|Leu| |
|135| | | |140| | | | |145| | | | | | | |
|AAG|GTT|ATT|CCG|GTG|TTC|AAT|GAG|AAC|GAT|GCC|GTT|AGT|ACC|AGG|AAG|528|
|Lys|Val|Ile|Pro|Val|Phe|Asn|Glu|Asn|Asp|Ala|Val|Ser|Thr|Arg|Lys| |
|150| | | |155| | | | |160| | | | | | | |
|GCT|CCC|TAT|GAG|GAT|TCT|TCT|GGT|ATA|TTT|TGG|GAT|AAT|GAT|AGT|TTA|576|
|Ala|Pro|Tyr|Glu|Asp|Ser|Ser|Gly|Ile|Phe|Trp|Asp|Asn|Asp|Ser|Leu| |
|165| | | |170| | | | |175| | | | | |180| |
|TCT|GCT|TTA|TTA|GCC|TTG|GAG|TTA|AAA|GCC|GAT|CTC|CTT|GTT|TTG|TTG|624|
|Ser|Ala|Leu|Leu|Ala|Leu|Glu|Leu|Lys|Ala|Asp|Leu|Leu|Val|Leu|Leu| |
|185| | | |190| | | | |195| | | | | | | |
|GAT|GTA|GAA|GGT|CTT|TAC|AGT|GGC|CCT|CCA|AGT|GAC|CCT|CAT|TCA| |672|
|Ser|Asp|Val|Glu|Gly|Leu|Tyr|Ser|Gly|Pro|Pro|Ser|Asp|Pro|His|Ser| |
|200| | | |205| | | | |210| | | | | | | |
|AAG|CTT|ATT|TAT|ACA|TAT|AAC|AAA|GAA|AAA|CAT|CAG|AAT|GAA|ATT|ACT|720|
|Lys|Leu|Ile|Tyr|Thr|Tyr|Asn|Lys|Glu|Lys|His|Gln|Asn|Glu|Ile|Thr| |
|215| | | |220| | | | |225| | | | | | | |
|TTT|GGC|GAC|AAG|TCT|AGA|GTG|GGA|AGA|GGC|GGA|ATG|ACT|GCC|AAA|GTA|768|
|Phe|Gly|Asp|Lys|Ser|Arg|Val|Gly|Arg|Gly|Gly|Met|Thr|Ala|Lys|Val| |
|230| | | |235| | | | |240| | | | | | | |
|AAA|GCT|GCG|GTT|CAT|GCA|GCT|GAA|GCT|GGC|ATT|CCT|GTT|GTT|ATT|ACC|816|
|Lys|Ala|Ala|Val|His|Ala|Ala|Glu|Ala|Gly|Ile|Pro|Val|Val|Ile|Thr| |
|245| | | |250| | | | |255| | | | | |260| |
|AGT|GGT|TTT|GCA|CCT|GAG|AAT|ATC|ATT|AAT|GTT|CTC|CAA|GGA|CAA|CGT|864|
|Ser|Gly|Phe|Ala|Pro|Glu|Asn|Ile|Ile|Asn|Val|Leu|Gln|Gly|Gln|Arg| |
|265| | | |270| | | | |275| | | | | | | |
|ATA|GGA|ACT|CTC|TTC|CAT|AAA|GAT|GCA|CAT|GAG|TGG|GCT|CAA|GTA|AAA|912|
|Ile|Gly|Thr|Leu|Phe|His|Lys|Asp|Ala|His|Glu|Trp|Ala|Gln|Val|Lys| |
|280| | | |285| | | | |290| | | | | | | |
|GAG|GTT|GAT|GCA|CGT|GAG|ATG|GCT|GTT|GCA|GCA|GGG|AAT|GTT|CGA|GAA|960|
|Glu|Val|Asp|Ala|Arg|Glu|Met|Ala|Val|Ala|Ala|Gly|Asn|Val|Arg|Glu| |
|295| | | |300| | | | |305| | | | | | | |
|TCC|AGG|CGT|TAT|CTT|CAG|AGG|AAA|GGA|AAC|AAA|ATT|TTA|CTT|AAA| |1008|
|Gly|Ser|Arg|Arg|Tyr|Leu|Gln|Arg|Lys|Gly|Asn|Lys|Ile|Leu|Leu|Lys| |
|310| | | |315| | | | |320| | | | | | | |
|ATA|GCT|GAT|GCC|CTG|GAA|GCA|AAT|GAA|AAA|ATA|ATC|AGG|ATT|GAA|AAT|1056|
|Ile|Ala|Asp|Ala|Leu|Glu|Ala|Asn|Glu|Lys|Ile|Ile|Arg|Ile|Glu|Asn| |

|     |     |     |     |     | 325 |     |     |     | 330 |     |     |     |     | 335 |     |     |     |     | 340 |      |
|-----|-----|-----|-----|-----|-----|-----|-----|-----|-----|-----|-----|-----|-----|-----|-----|-----|-----|-----|-----|------|
| GAA | GCT | GAT | GTT | ACT | GCT | GCA | CAA | GAA | GCA | GGA | TAT | GAA | AAA | TCC | TTG |     |     |     |     | 1104 |
| Ala | Asp | Val | Thr | Ala | Ala | Gln | Glu | Ala | Gly | Tyr | Glu | Lys | Ser | Leu |     |     |     |     |     |      |
| 345 |     |     |     |     | 350 |     |     |     | 355 |     |     |     |     |     |     |     |     |     |     |      |

```
GTG GCT AGG CTA GCT TTA AAA CCT GGG AAG ATT GCA AGT CTT GCA AAC         1152
Val Ala Arg Leu Ala Leu Lys Pro Gly Lys Ile Ala Ser Leu Ala Asn
360             365                 370

AAC ATG CGA ATC ATT GCC AAT ATG GAA GAT CCA ATT GGT CGA GTA TTA         1200
Met Arg Ile Ile Ala Asn Met Glu Asp Pro Ile Gly Arg Val Leu
375             380                 385

AAA CGT ACC GAG CTT TCA GAT GGG CTA ATT TTA GAA AAG ACA TCA TCT         1248
Lys Arg Thr Glu Leu Ser Asp Gly Leu Ile Leu Glu Lys Thr Ser Ser
390             395                 400

CCT TTG GGA GTG CTC CTT ATT GTT TTT GAG TCA CGT CCT GAT GCT CTT         1296
Pro Leu Gly Val Leu Leu Ile Val Phe Glu Ser Arg Pro Asp Ala Leu
405             410                 415                         420

GTA CAG ATA GCT TCA TTG GCA ATC CGA AGT GGG AAT GGG CTT CTC TTG         1344
Gln Ile Ala Ser Leu Ala Ile Arg Ser Gly Asn Gly Leu Leu Leu
425             430                 435

AAA GGT GGC AAA GAA GCT AAG CGA TCA AAT GCA ATT TTG CAC AAA GTA         1392
Lys Gly Gly Lys Glu Ala Lys Arg Ser Asn Ala Ile Leu His Lys Val
440             445                 450

ATT ATC GAG GCC ATA CCA GAT AAT GTT GGT GGA AAA CTT ATA GGA CTT         1440
Ile Ile Glu Ala Ile Pro Asp Asn Val Gly Gly Lys Leu Ile Gly Leu
455             460                 465

GTG ACC TCA AGG GAA GAG ATC CCT GAG CTA CTT AAG TTG GAT GAT GTA         1488
Val Thr Ser Arg Glu Glu Ile Pro Glu Leu Leu Lys Leu Asp Asp Val
470             475                 480

ATT GAT CTG GTA ATT CCA AGA GGC AGT AAC AAA CTT GTT TCT CAG ATC         1536
Ile Asp Leu Val Ile Pro Arg Gly Ser Asn Lys Leu Val Ser Gln Ile
485             490                 495                         500

AAG AGT TCA ACT AAA ATT CCT GTT TTA GGT CAT GCT GAT GGA ATT TGC         1584
Lys Ser Ser Thr Lys Ile Pro Val Leu Gly His Ala Asp Gly Ile Cys
505             510                 515

CAT GTC TAT GTT GAT AAG TCT GCT AAC GTG GAG ATG GCA AAG CGG ATT         1632
His Val Tyr Val Asp Lys Ser Ala Asn Val Glu Met Ala Lys Arg Ile
520             525                 530

GTA TTA GAT GCA AAA GTT GAT TAT CCG GCA GCC TGC AAT GCC ATG GAA         1680
Val Leu Asp Ala Lys Val Asp Tyr Pro Ala Ala Cys Asn Ala Met Glu
535             540                 545

ACA CTT CTT ATC CAC AAG GAT TTG ATA GAG AAA GGT TGG CTT AAG GAG         1728
Thr Leu Leu Ile His Lys Asp Leu Ile Glu Lys Gly Trp Leu Lys Glu
550             555                 560

ATC ATT CTT GAC CTT CGA ACT GAA GGC GTT ATA TTA TAT GGT GGC CCT         1776
Ile Ile Leu Asp Leu Arg Thr Glu Gly Val Ile Leu Tyr Gly Gly Pro
565             570                 575                         580

GTG GCA AGT TCT CTG TTA AAT ATT CCA CAA GCA CAT TCA TTT CAT CAT         1824
Val Ala Ser Ser Leu Leu Asn Ile Pro Gln Ala His Ser Phe His His
585             590                 595

GAG TAC AGT TCG CTG GCT TGC ACC GCC GAA ATT GTG GAT GAC GTG TAT         1872
Glu Tyr Ser Ser Leu Ala Cys Thr Ala Glu Ile Val Asp Asp Val Tyr
600             605                 610

GCA GCT ATT GAT CAT ATA AAT CTG TAT GGA AGT GCA CAT ACT GAT TCG         1920
Ala Ala Ile Asp His Ile Asn Leu Tyr Gly Ser Ala His Thr Asp Ser
615             620                 625

ATC GTT GCT GAA GAT AAC GAA GTA GCT AAT GTG TTT CTA CGC CAA GTA         1968
Ile Val Ala Glu Asp Asn Glu Val Ala Asn Val Phe Leu Arg Gln Val
630             635                 640

GAC AGT GCT GCT GTT TTT CAC AAT GCA AGC ACC AGA TTC AGT GAT GGG         2016
Asp Ser Ala Ala Val Phe His Asn Ala Ser Thr Arg Phe Ser Asp Gly
645             650                 655                         660
```

| | | |
|---|---|---|
| GCA CGA TTT GAG ACT AGG CGC AGA GGT TGG AAT TAGTACAAGC<br>Ala Arg Phe Glu Thr Arg Arg Arg Gly Trp Asn<br>665                    670 | | 2059 |
| AGGATTCATG CTCGAGGTCA GTAGGAGTTG AGGATTGTTA ACAACAAGAT | | 2109 |
| GGATACTAAA AGGAAGGGAC AAGTGGTAGA TGGTGATAGA GGCGTTGTCT | | 2159 |
| ACACCCACAA AGACCTTGCA ATTTAATTTT AATGGTGCTT TGATTCCTTT | | 2209 |
| TGTAGCCTTT TCGTTTGTTT TTTTTTTTC ACAGTAGAGA ACGGCATTTG | | 2259 |
| TACGGTTAAA TAAAACCGGG TAATTTATGT CATTATTTGC TTGTTCCTTT | | 2309 |
| TTGTCTAGAA TCTTTACTGT CAACAATTAT GGTCCACAAT GTTTAACGAT | | 2359 |
| TCTTGAATGA CTACAATTTC AATTTGAGTT AATTTTATA TGTAAAAAAA | | 2409 |
| AAAAAAAA | | 2417 |

We claim:

1. An isolated DNA molecule having the sequence of SEQ ID NO.: 1.

2. A cDNA clone encoding the enzyme of SEQ ID NO. 1, a bifunctional enzyme that has both gamma-glutamyl kinase and glutamic-gamma-semialdehyde dehydrogenase activities.

* * * * *

UNITED STATES PATENT AND TRADEMARK OFFICE
CERTIFICATE OF CORRECTION

PATENT NO. : 5,344,923
DATED : September 6, 1994
INVENTOR(S) : Desh P. S. Verma et al.

It is certified that error appears in the above-indentified patent and that said Letters Patent is hereby corrected as shown below:

Column 1, line 30, "which is delta$^1$-" should read --which is reduced by delta$^1$---. Column 2, line 32, "FIG. 1 is" should read --FIGS. 1A, 1B, 1C and 1D are--; line 38, after "(ProA)." insert --FIG. 1A and FIG. 1B show the first portion of the sequence and FIG. 1C and FIG. 1D show the latter portion of the sequence.--; line 39, "FIG. 2 is" should read --FIGS. 2A and 2B are--. Column 3, line 19, "FIG. 1" should read --FIGS. 1A, 1B, 1C and 1D--; line 24, "(FIG. 2)" should read --(FIGS. 2A and 2B)--; line 34, "proA of an ancestral gene;" should read --proA genes may have arisen in the bacteria by duplication of an ancestral gene;--; line 56, "FIG. 1" should read --FIGS. 1A, 1B, 1C and 1D--; line 60, "(see FIG. 2)" should read --(see FIGS. 2A and 2B)--. Column 4, line 7, after "inter-" insert --and--; line 9, "(FIG. 2)" should read --(FIGS. 2A and 2B)--; line 12, "FIG. 1" should read --FIGS. 1A, 1B, 1C and 1D--. Column 6, line 18, "#CSH26and" should read --#CSH26 and--; line 40, "Electro Cell Manipulator" should read --ELECTRO CELL MANIPULATOR--. Column 8, line 10, "Gene Screen" should read --GENE SCREEN--.

UNITED STATES PATENT AND TRADEMARK OFFICE
CERTIFICATE OF CORRECTION

PATENT NO. : 5,344,923

Page 2 of 7

DATED : September 6, 1994

INVENTOR(S) : Desh P. S. Verma et al

It is certified that error appears in the above-identified patent and that said Letters Patent is hereby corrected as shown below:

DELETE THE SEQUENCE LISTING IN COLUMN 7 THRU COLUMN 14 AND SUBSTITUTE THE ATTACH SHEETS.

Signed and Sealed this

Fourth Day of July, 1995

*Attest:*

BRUCE LEHMAN

*Attesting Officer*     *Commissioner of Patents and Trademarks*

(1) GENERAL INFORMATION:

(iii) NUMBER OF SEQUENCES: 1

(2) INFORMATION FOR SEQ ID NO: 1:
   (i) SEQUENCE CHARACTERISTICS:
      (A) LENGTH: 2417 base pairs
      (B) TYPE: nucleic acid
      (C) STRANDEDNESS: double stranded
      (D) TOPOLOGY: linear
   (ii) MOLECULE TYPE: cDNA
      (A) DESCRIPTION: Sequence encodes Pyrroline-5-carboxylate synthetase, a bifunctional enzyme consisting of glutamyl kinase and glutamyl semialdehyde dehydrogenase activities
   (v) FRAGMENT TYPE:
      N-terminus:                N-MESAVDPS--
      C-terminus:                --RRRGWN-C
      Internal Fragment:      --VDAREMAV--
   (vi) ORIGINAL SOURCE:
      (A) ORGANISM: Vigna aconitifolia
      (B) STRAIN: Mothbean
      (D) DEVELOPMENTAL STAGE: Root nodules
   (vii) IMMEDIATE SOURCE:
      (A) LIBRARY: cDNA expression library
      (B) CLONE: cDNA clone
   (x) PUBLICATION INFORMATION:

(A) AUTHORS: Chien-An A. Hu, Ashton J. Delauney and Desh Pal S. Verma
(B) TITLE: A bifunctional enzyme (delta1-pyrroline-5-carboxylate synthetase) catalyzes the first two steps in proline biosynthesis in plants
(C) JOURNAL: Proceeding of the National Academy of Science USA
(D) VOLUME: 89
(E) ISSUE: October
(F) PAGES: 9354-9358
(G) DATE: OCT-1992
(K) RELEVANT RESIDUES IN SEQ ID NO: 1: FROM position 37 to position 2049 GenBank M92276
(xi) SEQUENCE DESCRIPTION: SEQ ID NO: 1:

```
TGCTCTAAAG GCTATTGCTC GTATCAGTGC TCAGCC ATG GAG AGC GCG           48
                                        Met Glu Ser Ala
                                        1

GTG GAT CCT TCT CGG GGG TTC ATG AAG GAC GTG AAG CGT GTG ATC ATC    96
Val Asp Pro Ser Arg Gly Phe Met Lys Asp Val Lys Arg Val Ile Ile
 5               10                  15                  20

AAA GTT GGC ACC GCG GTG GTC ACT CGC GAA GAA GGA AGG TTA GCG GTT   144
Lys Val Gly Thr Ala Val Val Thr Arg Glu Glu Gly Arg Leu Ala Val
                 25                  30                  35

GGA AGA TTG GGA GCT CTG TGC GAG CAG ATT AAG CAA CTC AAC TCT CTC   192
Gly Arg Leu Gly Ala Leu Cys Glu Gln Ile Lys Gln Leu Asn Ser Leu
             40                  45                  50

GGA TAC GAC ATT ATA CTC GTC TCC TCT GGC CCC GTC GGT ATT GGA CGC   240
Gly Tyr Asp Ile Ile Leu Val Ser Ser Gly Pro Val Gly Ile Gly Arg
             55                  60                  65

CAA AGG CTA CGT TTC CGT AAA TTA ATC AAC AGC AGC TTC GCC GAC CTT   288
Gln Arg Leu Arg Phe Arg Lys Leu Ile Asn Ser Ser Phe Ala Asp Leu
         70                  75                  80

CAG AAA CCC CAA CTC GAA CTC GAC GGC AAG GCC TGC GCC GCC GTT GGA   336
Gln Lys Pro Gln Leu Glu Leu Asp Gly Lys Ala Cys Ala Ala Val Gly
 85                  90                  95                 100

CAG AAC AGT CTC ATG GCT CTC TAC GAT ACG CTG TTC ACT CAG CTC GAT   384
Gln Asn Ser Leu Met Ala Leu Tyr Asp Thr Leu Phe Thr Gln Leu Asp
                105                 110                 115

GTG ACA TCG GCT CAG CTT CTT GTG ACG GAT AAC GAT TTT CGA GAT AAG   432
Val Thr Ser Ala Gln Leu Leu Val Thr Asp Asn Asp Phe Arg Asp Lys
                120                 125                 130

GAT TTC AGG AAG CAG CTT ACT GAG ACT GTG AAG TCG CTG TTG GCG CTG   480
Asp Phe Arg Lys Gln Leu Thr Glu Thr Val Lys Ser Leu Leu Ala Leu
            135                 140                 145
```

```
AAG GTT ATT CCG GTG TTC AAT GAG AAC GAT GCC GTT AGT ACC AGG AAG    528
Lys Val Ile Pro Val Phe Asn Glu Asn Asp Ala Val Ser Thr Arg Lys
    150             155             160

GCT CCC TAT GAG GAT TCT TCT GGT ATA TTT TGG GAT AAT GAT AGT TTA    576
Ala Pro Tyr Glu Asp Ser Ser Gly Ile Phe Trp Asp Asn Asp Ser Leu
165             170             175             180

TCT GCT TTA TTA GCC TTG GAG TTA AAA GCC GAT CTC CTT GTT TTG TTG    624
Ser Ala Leu Leu Ala Leu Glu Leu Lys Ala Asp Leu Leu Val Leu Leu
                185             190             195

AGT GAT GTA GAA GGT CTT TAC AGT GGC CCT CCA AGT GAC CCT CAT TCA    672
Ser Asp Val Glu Gly Leu Tyr Ser Gly Pro Pro Ser Asp Pro His Ser
            200             205             210

AAG CTT ATT TAT ACA TAT AAC AAA GAA AAA CAT CAG AAT GAA ATT ACT    720
Lys Leu Ile Tyr Thr Tyr Asn Lys Glu Lys His Gln Asn Glu Ile Thr
        215             220             225

TTT GGC GAC AAG TCT AGA GTG GGA AGA GGC GGA ATG ACT GCC AAA GTA    768
Phe Gly Asp Lys Ser Arg Val Gly Arg Gly Gly Met Thr Ala Lys Val
    230             235             240

AAA GCT GCG GTT CAT GCA GCT GAA GCT GGC ATT CCT GTT GTT ATT ACC    816
Lys Ala Ala Val His Ala Ala Glu Ala Gly Ile Pro Val Val Ile Thr
245             250             255             260

AGT GGT TTT GCA CCT GAG AAT ATC ATT AAT GTT CTC CAA GGA CAA CGT    864
Ser Gly Phe Ala Pro Glu Asn Ile Ile Asn Val Leu Gln Gly Gln Arg
                265             270             275

ATA GGA ACT CTC TTC CAT AAA GAT GCA CAT GAG TGG GCT CAA GTA AAA    912
Ile Gly Thr Leu Phe His Lys Asp Ala His Glu Trp Ala Gln Val Lys
            280             285             290

GAG GTT GAT GCA CGT GAG ATG GCT GTT GCA GCA GGG AAT GTT CGA GAA    960
Glu Val Asp Ala Arg Glu Met Ala Val Ala Ala Gly Asn Val Arg Glu
        295             300             305

GGC TCC AGG CGT TAT CTT CAG AGG AAA GGA AAC AAA ATT TTA CTT AAA   1008
Gly Ser Arg Arg Tyr Leu Gln Arg Lys Gly Asn Lys Ile Leu Leu Lys
    310             315             320

ATA GCT GAT GCC CTG GAA GCA AAT GAA AAA ATA ATC AGG ATT GAA AAT   1056
Ile Ala Asp Ala Leu Glu Ala Asn Glu Lys Ile Ile Arg Ile Glu Asn
325             330             335             340

GAA GCT GAT GTT ACT GCT GCA CAA GAA GCA GGA TAT GAA AAA TCC TTG   1104
Glu Ala Asp Val Thr Ala Ala Gln Glu Ala Gly Tyr Glu Lys Ser Leu
                345             350             355

GTG GCT AGG CTA GCT TTA AAA CCT GGG AAG ATT GCA AGT CTT GCA AAC   1152
```

```
                Val Ala Arg Leu Ala Leu Lys Pro Gly Lys Ile Ala Ser Leu Ala Asn
                        360             365             370

AAC ATG CGA ATC ATT GCC AAT ATG GAA GAT CCA ATT GGT CGA GTA TTA    1200
Asn Met Arg Ile Ile Ala Asn Met Glu Asp Pro Ile Gly Arg Val Leu
        375             380             385

AAA CGT ACC GAG CTT TCA GAT GGG CTA ATT TTA GAA AAG ACA TCA TCT    1248
Lys Arg Thr Glu Leu Ser Asp Gly Leu Ile Leu Glu Lys Thr Ser Ser
        390             395             400

CCT TTG GGA GTG CTC CTT ATT GTT TTT GAG TCA CGT CCT GAT GCT CTT    1296
Pro Leu Gly Val Leu Leu Ile Val Phe Glu Ser Arg Pro Asp Ala Leu
405             410             415                     420

GTA CAG ATA GCT TCA TTG GCA ATC CGA AGT GGG AAT GGG CTT CTC TTG    1344
Val Gln Ile Ala Ser Leu Ala Ile Arg Ser Gly Asn Gly Leu Leu Leu
                425             430                     435

AAA GGT GGC AAA GAA GCT AAG CGA TCA AAT GCA ATT TTG CAC AAA GTA    1392
Lys Gly Gly Lys Glu Ala Lys Arg Ser Asn Ala Ile Leu His Lys Val
            440             445             450

ATT ATC GAG GCC ATA CCA GAT AAT GTT GGT GGA AAA CTT ATA GGA CTT    1440
Ile Ile Glu Ala Ile Pro Asp Asn Val Gly Gly Lys Leu Ile Gly Leu
            455             460             465

GTG ACC TCA AGG GAA GAG ATC CCT GAG CTA CTT AAG TTG GAT GAT GTA    1488
Val Thr Ser Arg Glu Glu Ile Pro Glu Leu Leu Lys Leu Asp Asp Val
        470             475             480

ATT GAT CTG GTA ATT CCA AGA GGC AGT AAC AAA CTT GTT TCT CAG ATC    1536
Ile Asp Leu Val Ile Pro Arg Gly Ser Asn Lys Leu Val Ser Gln Ile
485             490             495             500

AAG AGT TCA ACT AAA ATT CCT GTT TTA GGT CAT GCT GAT GGA ATT TGC    1584
Lys Ser Ser Thr Lys Ile Pro Val Leu Gly His Ala Asp Gly Ile Cys
            505             510             515

CAT GTC TAT GTT GAT AAG TCT GCT AAC GTG GAG ATG GCA AAG CGG ATT    1632
His Val Tyr Val Asp Lys Ser Ala Asn Val Glu Met Ala Lys Arg Ile
            520             525             530

GTA TTA GAT GCA AAA GTT GAT TAT CCG GCA GCC TGC AAT GCC ATG GAA    1680
Val Leu Asp Ala Lys Val Asp Tyr Pro Ala Ala Cys Asn Ala Met Glu
            535             540             545

ACA CTT CTT ATC CAC AAG GAT TTG ATA GAG AAA GGT TGG CTT AAG GAG    1728
Thr Leu Leu Ile His Lys Asp Leu Ile Glu Lys Gly Trp Leu Lys Glu
        550             555             560

ATC ATT CTT GAC CTT CGA ACT GAA GGC GTT ATA TTA TAT GGT GGC CCT    1776
Ile Ile Leu Asp Leu Arg Thr Glu Gly Val Ile Leu Tyr Gly Gly Pro
565             570             575             580
```

```
GTG GCA AGT TCT CTG TTA AAT ATT CCA CAA GCA CAT TCA TTT CAT CAT    1824
Val Ala Ser Ser Leu Leu Asn Ile Pro Gln Ala His Ser Phe His His
                585             590                 595

GAG TAC AGT TCG CTG GCT TGC ACC GCC GAA ATT GTG GAT GAC GTG TAT    1872
Glu Tyr Ser Ser Leu Ala Cys Thr Ala Glu Ile Val Asp Asp Val Tyr
                600             605                 610

GCA GCT ATT GAT CAT ATA AAT CTG TAT GGA AGT GCA CAT ACT GAT TCG    1920
Ala Ala Ile Asp His Ile Asn Leu Tyr Gly Ser Ala His Thr Asp Ser
            615             620                 625

ATC GTT GCT GAA GAT AAC GAA GTA GCT AAT GTG TTT CTA CGC CAA GTA    1968
Ile Val Ala Glu Asp Asn Glu Val Ala Asn Val Phe Leu Arg Gln Val
        630             635                 640

GAC AGT GCT GCT GTT TTT CAC AAT GCA AGC ACC AGA TTC AGT GAT GGG    2016
Asp Ser Ala Ala Val Phe His Asn Ala Ser Thr Arg Phe Ser Asp Gly
645             650                 655                 660

GCA CGA TTT GAG ACT AGG CGC AGA GGT TGG AAT TAGTACAAGC             2059
Ala Arg Phe Glu Thr Arg Arg Arg Gly Trp Asn
            665             670

AGGATTCATG CTCGAGGTCA GTAGGAGTTG AGGATTGTTA ACAACAAGAT             2109

GGATACTAAA AGGAAGGGAC AAGTGGTAGA TGGTGATAGA GGCGTTGTCT             2159

ACACCCACAA AGACCTTGCA ATTTAATTTT AATGGTGCTT TGATTCCTTT             2209

TGTAGCCTTT TCGTTTGTTT TTTTTTTTTC ACAGTAGAGA ACGGCATTTG             2259

TACGGTTAAA TAAAACCGGG TAATTTATGT CATTATTTGC TTGTTCCTTT             2309

TTGTCTAGAA TCTTTACTGT CAACAATTAT GGTCCACAAT GTTTAACGAT             2359

TCTTGAATGA CTACAATTTC AATTTGAGTT AATTTTTATA TGTAAAAAAA             2409

AAAAAAAA                                                           2417
```